US012603177B2

(12) United States Patent
Sayapaneni et al.

(10) Patent No.: US 12,603,177 B2
(45) Date of Patent: Apr. 14, 2026

(54) INTERACTIVE CONVERSATIONAL SYMPTOM CHECKER

(71) Applicant: Walmart Apollo, LLC, Bentonville, AR (US)

(72) Inventors: Phani Ram Sayapaneni, Sunnyvale, CA (US); Navin Naidu, Dublin, CA (US); Venkata Naga Vamsi Krishna Nandanavanam, Newark, CA (US); Shankara Bhargava, Santa Clara, CA (US)

(73) Assignee: Walmart Apollo, LLC, Bentonville, AR (US)

( * ) Notice: Subject to any disclaimer, the term of this patent is extended or adjusted under 35 U.S.C. 154(b) by 364 days.

(21) Appl. No.: 18/100,645

(22) Filed: Jan. 24, 2023

(65) Prior Publication Data

US 2023/0245774 A1     Aug. 3, 2023

Related U.S. Application Data

(60) Provisional application No. 63/304,834, filed on Jan. 31, 2022.

(51) Int. Cl.
G16H 50/20          (2018.01)
G06F 40/20          (2020.01)
          (Continued)

(52) U.S. Cl.
CPC ............. G16H 50/20 (2018.01); G06F 40/20 (2020.01); G06F 40/279 (2020.01); G06F 40/40 (2020.01); G16H 40/20 (2018.01)

(58) Field of Classification Search
CPC ........ G16H 50/20; G16H 50/00; G16H 40/20; G06F 40/20; G06F 40/279
See application file for complete search history.

(56) References Cited

U.S. PATENT DOCUMENTS 6,764,447 B2     7/2004   Iliff
7,149,756 B1 *  12/2006   Schmitt ................. G16H 50/20
          (Continued)

FOREIGN PATENT DOCUMENTS

CN          109243600 A     11/2020
CN          115132350 A     9/2022

OTHER PUBLICATIONS

Apotheka Systems Inc, "Apothēka Patient" mobile application 2019, Apple App Store Preview, 3 pgs, retrieved from https://apps.apple.com/US/app/apoth%C4%93ka-patient/id1454086094 on Jun. 20, 2025.

*Primary Examiner* — Samuel G Neway
(74) *Attorney, Agent, or Firm* — DICKINSON WRIGHT RLLP; Hector A. Agdeppa

(57)          ABSTRACT

A system including one or more processors and one or more non-transitory computer-readable media storing computing instructions that, when executed on the one or more processors, cause the one or more processors to perform: receiving text from a user; generating, from an undirected graph, a subgraph mapping the one or more symptoms to connected diseases; calculating a respective posterior probability for each of the connected diseases using the subgraph and evidence to formulate a hypothesis diagnosis; iteratively: determining one or more questions to send the user based on a set of top symptoms for the hypothesis diagnosis; sending the one or more questions to the user; receiving one or more responses from the user; and updating the hypothesis diagnosis; and sending a recommendation to the user to schedule an appointment with a provider for the hypothesis diagnosis. Other embodiments are disclosed.

14 Claims, 7 Drawing Sheets

(51) Int. Cl.
    *G06F 40/279*       (2020.01)
    *G06F 40/40*        (2020.01)
    *G16H 40/20*       (2018.01)

(56)               References Cited

U.S. PATENT DOCUMENTS

| | | | | |
|---|---|---|---|---|
| 2007/0167687 | A1* | 7/2007 | Bertolero | G16H 10/20 |
| | | | | 128/920 |
| 2008/0177578 | A1* | 7/2008 | Zakim | G16H 50/30 |
| | | | | 705/3 |
| 2013/0268203 | A1* | 10/2013 | Pyloth | G16H 50/20 |
| | | | | 702/19 |
| 2014/0012790 | A1* | 1/2014 | Oberkampf | G16H 50/20 |
| | | | | 706/46 |
| 2014/0122109 | A1* | 5/2014 | Ghanbari | G16H 10/20 |
| | | | | 705/2 |
| 2017/0344711 | A1* | 11/2017 | Liu | G06N 5/022 |
| 2018/0011856 | A1* | 1/2018 | Li | G16H 70/60 |
| 2018/0011979 | A1* | 1/2018 | Zhong | G16H 10/20 |
| 2018/0060510 | A1* | 3/2018 | Baldauf | G16H 50/20 |
| 2018/0322954 | A1* | 11/2018 | Ding | G16H 70/60 |
| 2019/0252074 | A1* | 8/2019 | Datla | G06F 17/10 |
| 2020/0185102 | A1 | 6/2020 | Leventhal et al. | |
| 2020/0265955 | A1* | 8/2020 | Corapi | G06N 7/01 |
| 2020/0279647 | A1* | 9/2020 | Buchard | G16H 10/20 |
| 2021/0192365 | A1* | 6/2021 | Zhang | G06N 5/022 |
| 2021/0287800 | A1* | 9/2021 | Ghosh | G16H 10/60 |
| 2023/0044314 | A1* | 2/2023 | Mitteldorf | G06T 11/206 |
| 2023/0245774 | A1* | 8/2023 | Sayapaneni | G16H 80/00 |
| | | | | 704/9 |

* cited by examiner

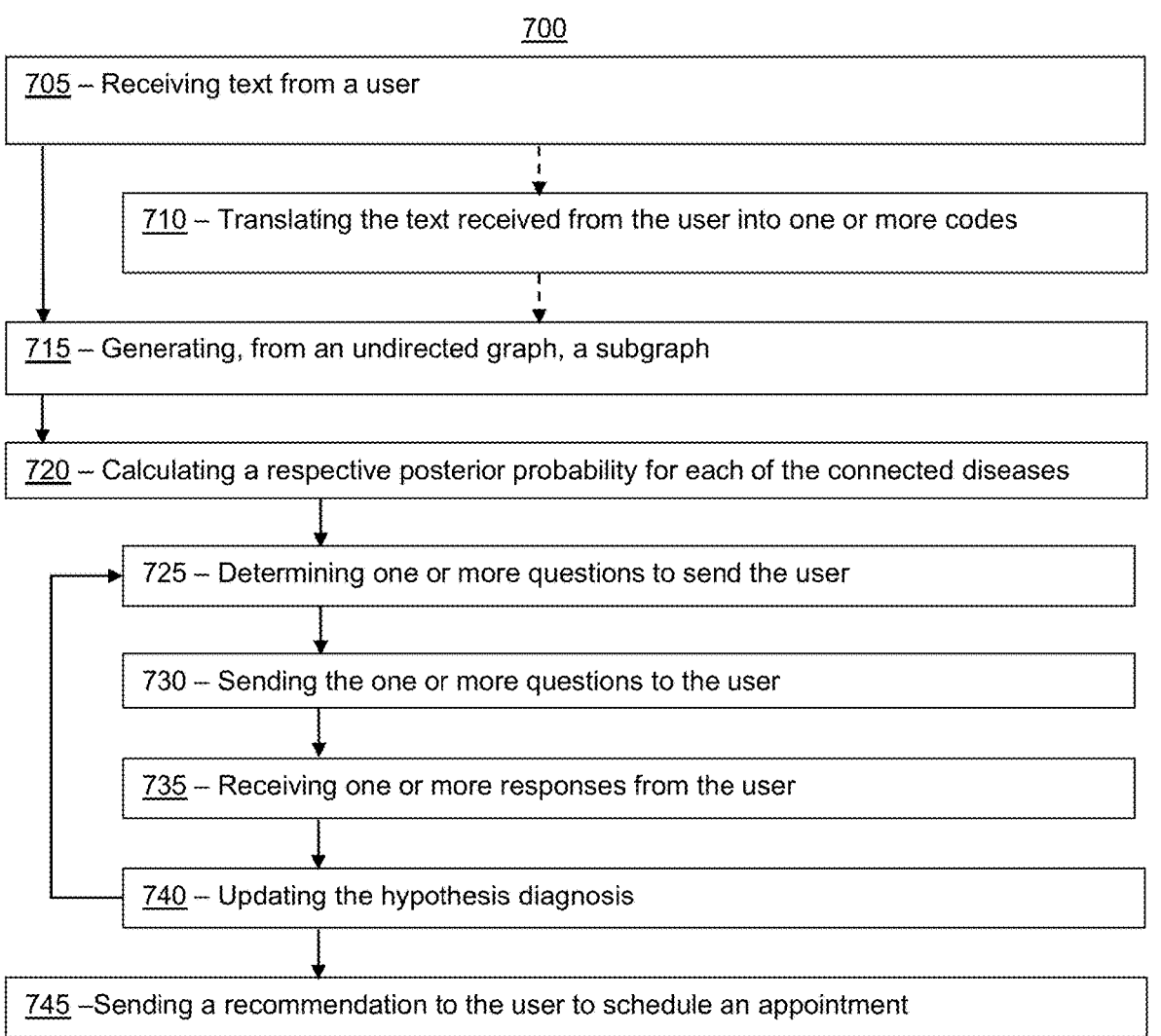

700

705 – Receiving text from a user

710 – Translating the text received from the user into one or more codes

715 – Generating, from an undirected graph, a subgraph

720 – Calculating a respective posterior probability for each of the connected diseases 725 – Determining one or more questions to send the user 730 – Sending the one or more questions to the user 735 – Receiving one or more responses from the user 740 – Updating the hypothesis diagnosis 745 –Sending a recommendation to the user to schedule an appointment

FIG. 7

INTERACTIVE CONVERSATIONAL SYMPTOM CHECKER

CROSS-REFERENCE TO RELATED APPLICATIONS

This application is a non-provisional application that claims priority to U.S. Provisional Application No. 63/304,834, filed Jan. 31, 2022. U.S. Provisional Application No. 63/304,834 is incorporated herein by reference in its entirety.

TECHNICAL FIELD

This disclosure relates generally to an interactive conversational symptom checker.

BACKGROUND

Generally, symptom checkers can be web-based applications where a user selects symptoms from a list of generalized symptoms and options. Frequently, many symptoms of the user in the list of generalized symptoms can be missing or part of another list not viewed from the options and/or from a drop down menu. Operating these types of symptom checkers can be time consuming and inefficient for the user.

BRIEF DESCRIPTION OF THE DRAWINGS

To facilitate further description of the embodiments, the following drawings are provided in which:

FIG. 7 illustrates a flow chart for a method, according to another embodiment.

Figure 1:
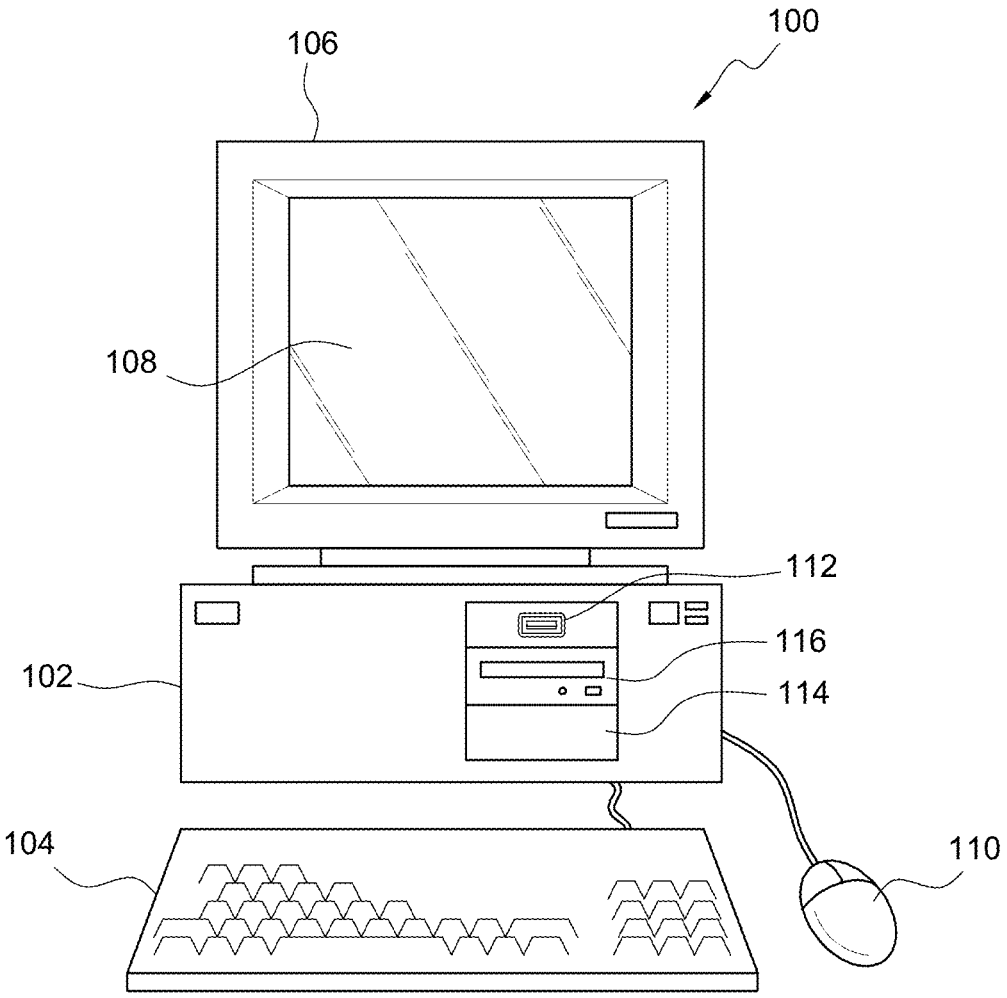
FIG. 1 illustrates a front elevational view of a computer system that is suitable for implementing an embodiment of the system disclosed in FIG. 3.

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

The terms "couple," "coupled," "couples," "coupling," and the like should be broadly understood and refer to connecting two or more elements mechanically and/or otherwise. Two or more electrical elements may be electrically coupled together, but not be mechanically or otherwise coupled together. Coupling may be for any length of time, e.g., permanent or semi-permanent or only for an instant. "Electrical coupling" and the like should be broadly understood and include electrical coupling of all types. The absence of the word "removably," "removable," and the like near the word "coupled," and the like does not mean that the coupling, etc. in question is or is not removable.

As defined herein, two or more elements are "integral" if they are comprised of the same piece of material. As defined herein, two or more elements are "non-integral" if each is comprised of a different piece of material.

As defined herein, "approximately" can, in some embodiments, mean within plus or minus ten percent of the stated value. In many embodiments, "approximately" can mean within plus or minus five percent of the stated value. In further embodiments, "approximately" can mean within plus or minus three percent of the stated value. In yet many embodiments, "approximately" can mean within plus or minus one percent of the stated value.

DESCRIPTION OF EXAMPLES OF EMBODIMENTS

Figure 2:
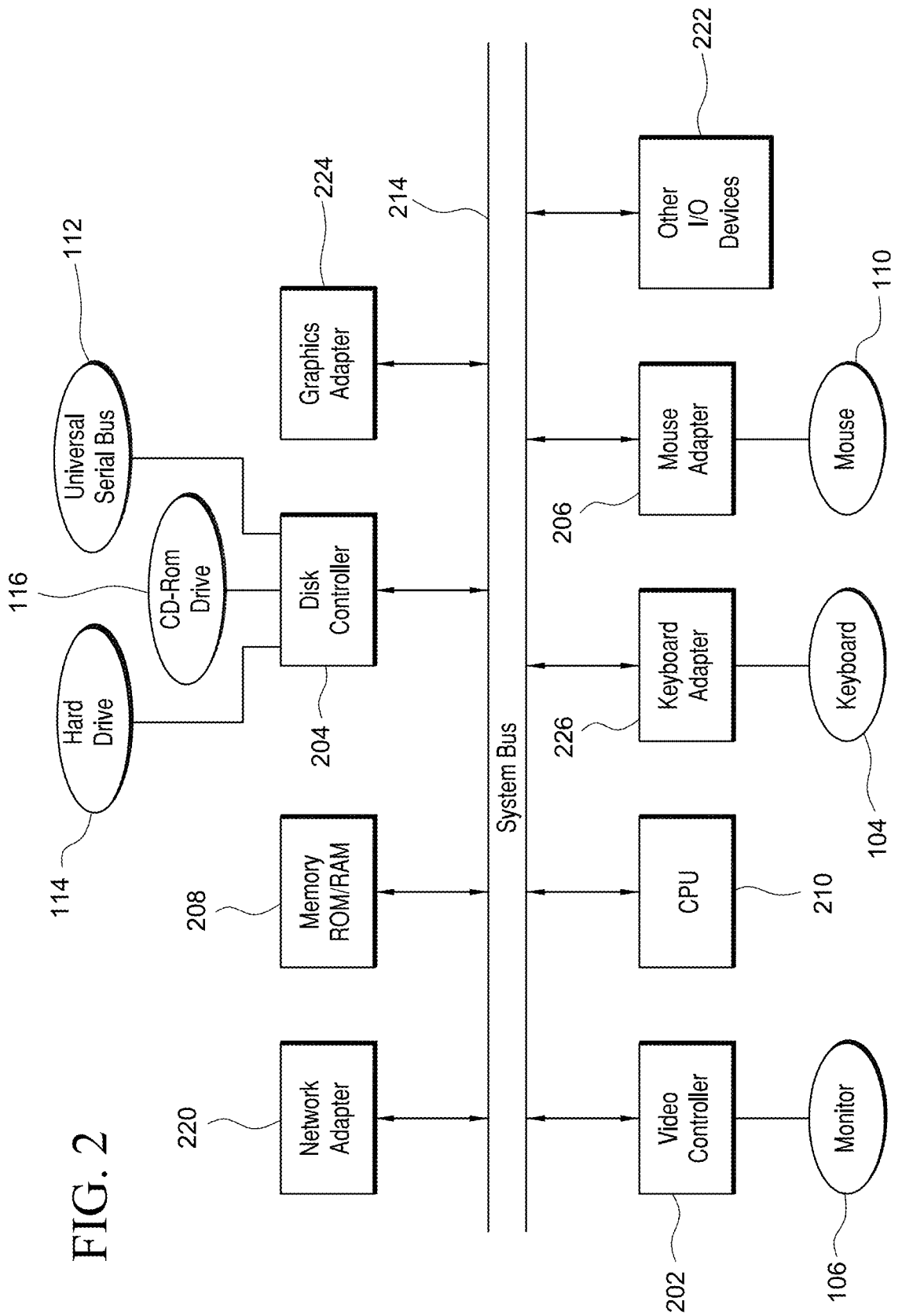
FIG. 2 illustrates a representative block diagram of an example of the elements included in the circuit boards inside a chassis of the computer system of FIG. 1.

Turning to the drawings, FIG. 1 illustrates an exemplary embodiment of a computer system 100, all of which or a portion of which can be suitable for (i) implementing part or all of one or more embodiments of the techniques, methods, and systems and/or (ii) implementing and/or operating part or all of one or more embodiments of the non-transitory computer readable media described herein. As an example, a different or separate one of computer system 100 (and its internal components, or one or more elements of computer system 100) can be suitable for implementing part or all of the techniques described herein. Computer system 100 can comprise chassis 102 containing one or more circuit boards (not shown), a Universal Serial Bus (USB) port 112, a Compact Disc Read-Only Memory (CD-ROM) and/or Digital Video Disc (DVD) drive 116, and a hard drive 114. A representative block diagram of the elements included on the circuit boards inside chassis 102 is shown in FIG. 2. A central processing unit (CPU) 210 in FIG. 2 is coupled to a system bus 214 in FIG. 2. In various embodiments, the architecture of CPU 210 can be compliant with any of a variety of commercially distributed architecture families.

Continuing with FIG. 2, system bus 214 also is coupled to memory storage unit 208 that includes both read only memory (ROM) and random access memory (RAM). Non-volatile portions of memory storage unit 208 or the ROM can be encoded with a boot code sequence suitable for restoring computer system 100 (FIG. 1) to a functional state after a system reset. In addition, memory storage unit 208 can include microcode such as a Basic Input-Output System (BIOS). In some examples, the one or more memory storage units of the various embodiments disclosed herein can include memory storage unit 208, a USB-equipped electronic device (e.g., an external memory storage unit (not shown) coupled to universal serial bus (USB) port 112 (FIGS. 1-2), hard drive 114 (FIGS. 1-2), and/or CD-ROM, DVD, Blu-Ray, or other suitable media, such as media configured to be used in CD-ROM and/or DVD drive 116 (FIGS. 1-2). Non-volatile or non-transitory memory storage unit(s) refer to the portions of the memory storage units(s) that are non-volatile memory and not a transitory signal. In the same or different examples, the one or more memory storage units of the various embodiments disclosed herein can include an operating system, which can be a software program that manages the hardware and software resources of a computer and/or a computer network. The operating system can perform basic tasks such as, for example, controlling and allocating memory, prioritizing the processing of instructions, controlling input and output devices, facilitating networking, and managing files. Exemplary operating systems can includes one or more of the following: (i) Microsoft® Windows® operating system (OS) by Microsoft Corp. of Redmond, Washington, United States of America, (ii) Mac® OS X by Apple Inc. of Cupertino, California, United States of America, (iii) UNIX® OS, and (iv) Linux® OS. Further exemplary operating systems can comprise one of the following: (i) the iOS® operating system by Apple Inc. of Cupertino, California, United States of America, (ii) the Blackberry® operating system by Research In Motion (RIM) of Waterloo, Ontario, Canada, (iii) the WebOS operating system by LG Electronics of Seoul, South Korea, (iv) the Android™ operating system developed by Google, of Mountain View, California, United States of America, (v) the Windows Mobile™ operating system by Microsoft Corp. of Redmond, Washington, United States of America, or (vi) the Symbian™ operating system by Accenture PLC of Dublin, Ireland.

As used herein, "processor" and/or "processing module" means any type of computational circuit, such as but not limited to a microprocessor, a microcontroller, a controller, a complex instruction set computing (CISC) microprocessor, a reduced instruction set computing (RISC) microprocessor, a very long instruction word (VLIW) microprocessor, a graphics processor, a digital signal processor, or any other type of processor or processing circuit capable of performing the desired functions. In some examples, the one or more processors of the various embodiments disclosed herein can comprise CPU 210.

In the depicted embodiment of FIG. 2, various I/O devices such as a disk controller 204, a graphics adapter 224, a video controller 202, a keyboard adapter 226, a mouse adapter 206, a network adapter 220, and other I/O devices 222 can be coupled to system bus 214. Keyboard adapter 226 and mouse adapter 206 are coupled to a keyboard 104 (FIGS. 1-2) and a mouse 110 (FIGS. 1-2), respectively, of computer system 100 (FIG. 1). While graphics adapter 224 and video controller 202 are indicated as distinct units in FIG. 2, video controller 202 can be integrated into graphics adapter 224, or vice versa in other embodiments. Video controller 202 is suitable for refreshing a monitor 106 (FIGS. 1-2) to display images on a screen 108 (FIG. 1) of computer system 100 (FIG. 1). Disk controller 204 can control hard drive 114 (FIGS. 1-2), USB port 112 (FIGS. 1-2), and CD-ROM and/or DVD drive 116 (FIGS. 1-2). In other embodiments, distinct units can be used to control each of these devices separately.

In some embodiments, network adapter 220 can comprise and/or be implemented as a WNIC (wireless network interface controller) card (not shown) plugged or coupled to an expansion port (not shown) in computer system 100 (FIG. 1). In other embodiments, the WNIC card can be a wireless network card built into computer system 100 (FIG. 1). A wireless network adapter can be built into computer system 100 (FIG. 1) by having wireless communication capabilities integrated into the motherboard chipset (not shown), or implemented via one or more dedicated wireless communication chips (not shown), connected through a PCI (peripheral component interconnector) or a PCI express bus of computer system 100 (FIG. 1) or USB port 112 (FIG. 1). In other embodiments, network adapter 220 can comprise and/or be implemented as a wired network interface controller card (not shown).

Although many other components of computer system 100 (FIG. 1) are not shown, such components and their interconnection are well known to those of ordinary skill in the art. Accordingly, further details concerning the construction and composition of computer system 100 (FIG. 1) and the circuit boards inside chassis 102 (FIG. 1) are not discussed herein.

When computer system 100 in FIG. 1 is running, program instructions stored on a USB drive in USB port 112, on a CD-ROM or DVD in CD-ROM and/or DVD drive 116, on hard drive 114, or in memory storage unit 208 (FIG. 2) are executed by CPU 210 (FIG. 2). A portion of the program instructions, stored on these devices, can be suitable for carrying out all or at least part of the techniques described herein. In various embodiments, computer system 100 can be reprogrammed with one or more modules, system, applications, and/or databases, such as those described herein, to convert a general purpose computer to a special purpose computer. For purposes of illustration, programs and other executable program components are shown herein as discrete systems, although it is understood that such programs and components may reside at various times in different storage components of computing device 100, and can be executed by CPU 210. Alternatively, or in addition to, the systems and procedures described herein can be implemented in hardware, or a combination of hardware, software, and/or firmware. For example, one or more application specific integrated circuits (ASICs) can be programmed to carry out one or more of the systems and procedures described herein. For example, one or more of the programs and/or executable program components described herein can be implemented in one or more ASICs.

Although computer system 100 is illustrated as a desktop computer in FIG. 1, there can be examples where computer system 100 may take a different form factor while still having functional elements similar to those described for computer system 100. In some embodiments, computer system 100 may comprise a single computer, a single server, or a cluster or collection of computers or servers, or a cloud of computers or servers. Typically, a cluster or collection of servers can be used when the demand on computer system 100 exceeds the reasonable capability of a single server or computer. In certain embodiments, computer system 100 may comprise a portable computer, such as a laptop computer. In certain other embodiments, computer system 100 may comprise a mobile device, such as a smartphone. In certain additional embodiments, computer system 100 may comprise an embedded system.

Figure 3:
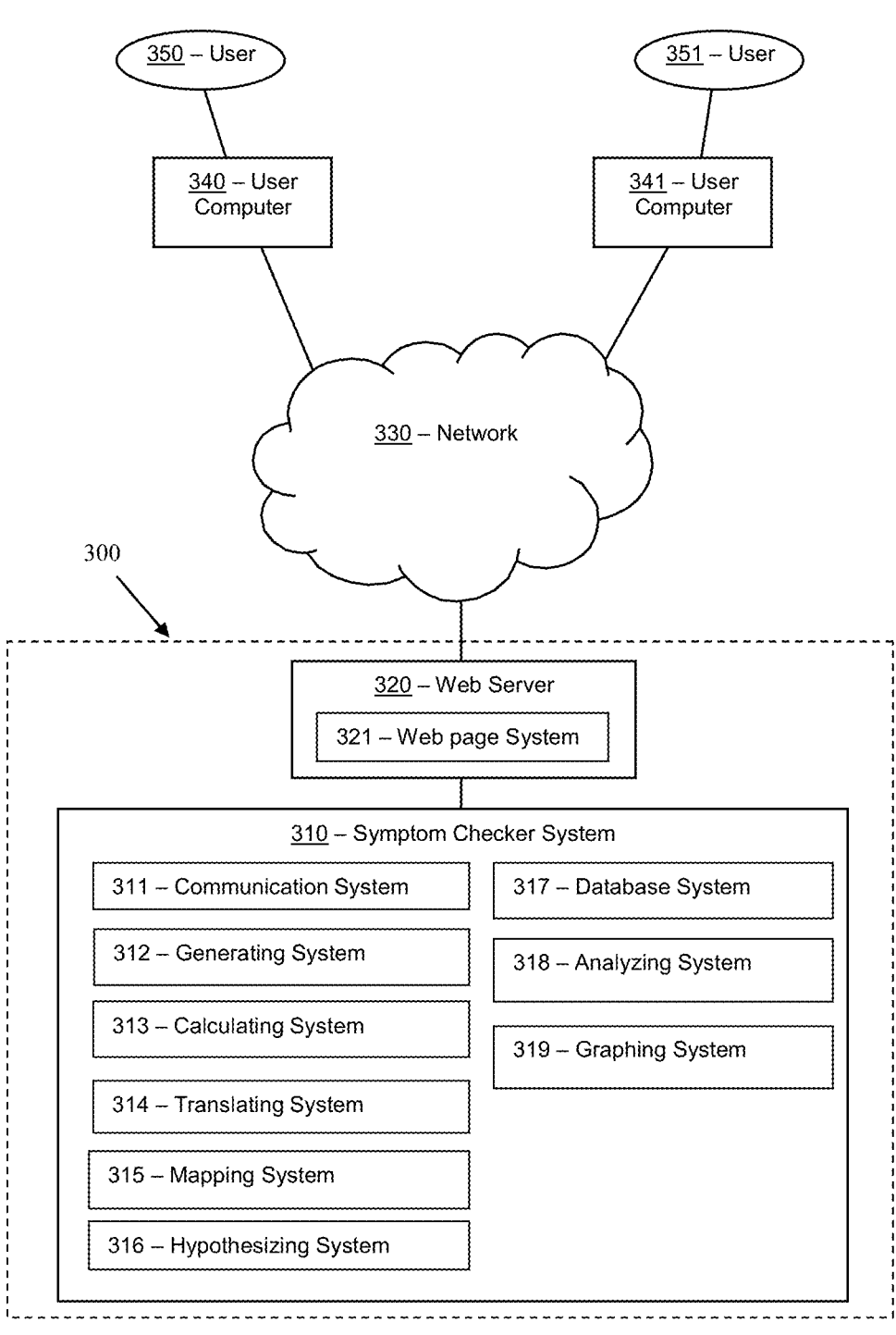
FIG. 3 illustrates a block diagram of a system that can be employed for utilizing conversational artificial intelligence, according to an embodiment.

Turning ahead in the drawings, FIG. 3 illustrates a block diagram of a system 300 that can be employed for utilizing conversational artificial intelligence to formulate one or more questions in response to symptoms disclosed by a user via an online platform. System 300 can include generating one or more iterations of hypotheses based on additional symptoms received from the user during a guided conversation with the conversational artificial intelligence. System 300 is merely exemplary and embodiments of the system are not limited to the embodiments presented herein. The system can be employed in many different embodiments or examples not specifically depicted or described herein. In some embodiments, certain elements, modules, or systems of system 300 can perform various procedures, processes, and/or activities. In other embodiments, the procedures, processes, and/or activities can be performed by other suitable elements, modules, or systems of system 300. System 300 can be implemented with hardware and/or software, as described herein. In some embodiments, part or all of the hardware and/or software can be conventional, while in these or other embodiments, part or all of the hardware and/or software can be customized (e.g., optimized) for implementing part or all of the functionality of system 300 described herein.

In many embodiments, system 300 can include a symptom checker system 310 and/or a web server 320. Symptom checker system 310 and/or web server 320 can each be a computer system, such as computer system 100 (FIG. 1), as described above, and can each be a single computer, a single server, or a cluster or collection of computers or servers, or a cloud of computers or servers. In another embodiment, a single computer system can host two or more of, or all of, symptom checker system 310 and/or web server 320. Additional details regarding symptom checker system 310 and/or web server 320 are described herein.

In a number of embodiments, each of symptom checker system 310 and/or web server 320 can be a special-purpose computer programed specifically to perform specific functions not associated with a general-purpose computer, as described in greater detail below.

In some embodiments, web server 320 can be in data communication through network 330 with one or more user computers, such as user computers 340 and/or 341. Network 330 can be a public network (such as the Internet), a private network or a hybrid network. In some embodiments, user computers 340-341 can be used by users, such as users 350 and 351, which also can be referred to as users, patients, and/or customers, in which case, user computers 340 and 341 can be referred to as patient computers. In many embodiments, web server 320 can host one or more sites (e.g., websites) that allow users to interact by texting or conversing with a conversational artificial intelligence or a chat bot ("bot") via an online platform and receive a hypothesis diagnosis and/or a recommendation to schedule an appointment with a provider, in addition to other suitable activities. In several embodiments, web server 320 can include a web page system 321.

In some embodiments, an internal network that is not open to the public can be used for communications between symptom checker system 310 and/or web server 320 within system 300. Accordingly, in some embodiments, symptom checker system 310 (and/or the software used by such systems) can refer to a back end of system 300, which can be operated by an operator and/or administrator of system 300, and web server 320 (and/or the software used by such system) can refer to a front end of system 300, and can be accessed and/or used by one or more users, such as users 350-351, using user computers 340-341, respectively. In these or other embodiments, the operator and/or administrator of system 300 can manage system 300, the processor(s) of system 300, and/or the memory storage unit(s) of system 300 using the input device(s) and/or display device(s) of system 300.

In certain embodiments, user computers 340-341 can be desktop computers, laptop computers, a mobile device, and/or other endpoint devices used by one or more users 350 and 351, respectively. A mobile device can refer to a portable electronic device (e.g., an electronic device easily conveyable by hand by a person of average size) with the capability to present audio and/or visual data (e.g., text, images, videos, music, etc.). For example, a mobile device can include at least one of a digital media player, a cellular telephone (e.g., a smartphone), a personal digital assistant, a handheld digital computer device (e.g., a tablet personal computer device), a laptop computer device (e.g., a notebook computer device, a netbook computer device), a wearable user computer device, or another portable computer device with the capability to present audio and/or visual data (e.g., images, videos, music, etc.). Thus, in many examples, a mobile device can include a volume and/or weight sufficiently small as to permit the mobile device to be easily conveyable by hand. For examples, in some embodiments, a mobile device can occupy a volume of less than or equal to approximately 1790 cubic centimeters, 2434 cubic centimeters, 2876 cubic centimeters, 4056 cubic centimeters, and/or 5752 cubic centimeters. Further, in these embodiments, a mobile device can weigh less than or equal to 15.6 Newtons, 17.8 Newtons, 22.3 Newtons, 31.2 Newtons, and/or 44.5 Newtons.

Exemplary mobile devices can include (i) an iPod®, iPhone®, iTouch®, iPad®, MacBook® or similar product by Apple Inc. of Cupertino, California, United States of America, (ii) a Blackberry® or similar product by Research in Motion (RIM) of Waterloo, Ontario, Canada, (iii) a Lumia® or similar product by the Nokia Corporation of Keilaniemi, Espoo, Finland, and/or (iv) a Galaxy™ or similar product by the Samsung Group of Samsung Town, Seoul, South Korea. Further, in the same or different embodiments, a mobile device can include an electronic device configured to implement one or more of (i) the iPhone® operating system by Apple Inc. of Cupertino, California, United States of America, (ii) the Blackberry® operating system by Research In Motion (RIM) of Waterloo, Ontario, Canada, (iii) the Palm® operating system by Palm, Inc. of Sunnyvale, California, United States, (iv) the Android™ operating system developed by the Open Handset Alliance, (v) the Windows Mobile™ operating system by Microsoft Corp. of Redmond, Washington, United States of America, or (vi) the Symbian™ operating system by Nokia Corp. of Keilaniemi, Espoo, Finland.

Further still, the term "wearable user computer device" as used herein can refer to an electronic device with the capability to present audio and/or visual data (e.g., text, images, videos, music, etc.) that is configured to be worn by a user and/or mountable (e.g., fixed) on the user of the wearable user computer device (e.g., sometimes under or over clothing; and/or sometimes integrated with and/or as clothing and/or another accessory, such as, for example, a hat, eyeglasses, a wrist watch, shoes, etc.). In many examples, a wearable user computer device can include a mobile device, and vice versa. However, a wearable user computer device does not necessarily include a mobile device, and vice versa.

In specific examples, a wearable user computer device can include a head mountable wearable user computer device (e.g., one or more head mountable displays, one or more eyeglasses, one or more contact lenses, one or more retinal displays, etc.) or a limb mountable wearable user computer device (e.g., a smart watch). In these examples, a head mountable wearable user computer device can be mountable in close proximity to one or both eyes of a user of the head mountable wearable user computer device and/or vectored in alignment with a field of view of the user.

In more specific examples, a head mountable wearable user computer device can include (i) Google Glass™ product or a similar product by Google Inc. of Menlo Park, California, United States of America; (ii) the Eye Tap™ product, the Laser Eye Tap™ product, or a similar product by ePI Lab of Toronto, Ontario, Canada, and/or (iii) the Raptyr™ product, the STAR 1200™ product, the Vuzix Smart Glasses M100™ product, or a similar product by Vuzix Corporation of Rochester, New York, United States of America. In other specific examples, a head mountable wearable user computer device can include the Virtual Retinal Display™ product, or similar product by the University of Washington of Seattle, Washington, United States of America. Meanwhile, in further specific examples, a limb mountable wearable user computer device can include the iWatch™ product, or similar product by Apple Inc. of Cupertino, California, United States of America, the Galaxy Gear or similar product of Samsung Group of Samsung Town, Seoul, South Korea, the Moto 360 product or similar product of Motorola of Schaumburg, Illinois, United States of America, and/or the Zip™ product, One™ product, Flex™ product, Charge™ product, Surge™ product, or similar product by Fitbit Inc. of San Francisco, California, United States of America.

Meanwhile, in many embodiments, system 300 also can be configured to communicate with and/or include one or more databases, such as database system 317. The one or more databases can include a medical concept database that contains information about diseases, symptoms, or other suitable medical concepts, for example, among other data, such as described herein in further detail. The one or more databases can be stored on one or more memory storage units (e.g., non-transitory computer readable media), which can be similar or identical to the one or more memory storage units (e.g., non-transitory computer readable media) described above with respect to computer system 100 (FIG. 1). Also, in some embodiments, for any particular database of the one or more databases, that particular database can be stored on a single memory storage unit or the contents of that particular database can be spread across multiple ones of the memory storage units storing the one or more databases, depending on the size of the particular database and/or the storage capacity of the memory storage units.

The one or more databases can each include a structured (e.g., indexed) collection of data and can be managed by any suitable database management systems configured to define, create, query, organize, update, and manage database(s). Exemplary database management systems can include MySQL (Structured Query Language) Database, PostgreSQL Database, Microsoft SQL Server Database, Oracle Database, SAP (Systems, Applications, & Products) Database, and IBM DB2 Database.

In many embodiments, symptom checker system 310 can include a communication system 311, a generating system 312, a calculating system 313, a translating system 314, a mapping system 315, a hypothesizing system 316, database system 317, an analyzing system 318, and/or a graphing system 319. In many embodiments, the systems of symptom checker system 310 can be modules of computing instructions (e.g., software modules) stored at non-transitory computer readable media that operate on one or more processors. In other embodiments, the systems of symptom checker system 310 can be implemented in hardware. Symptom checker system 310 can be a computer system, such as computer system 100 (FIG. 1), as described above, and can be a single computer, a single server, or a cluster or collection of computers or servers, or a cloud of computers or servers. In another embodiment, a single computer system can host symptom checker system 310. Additional details regarding symptom checker system 310 and the components thereof are described herein.

Figure 4:
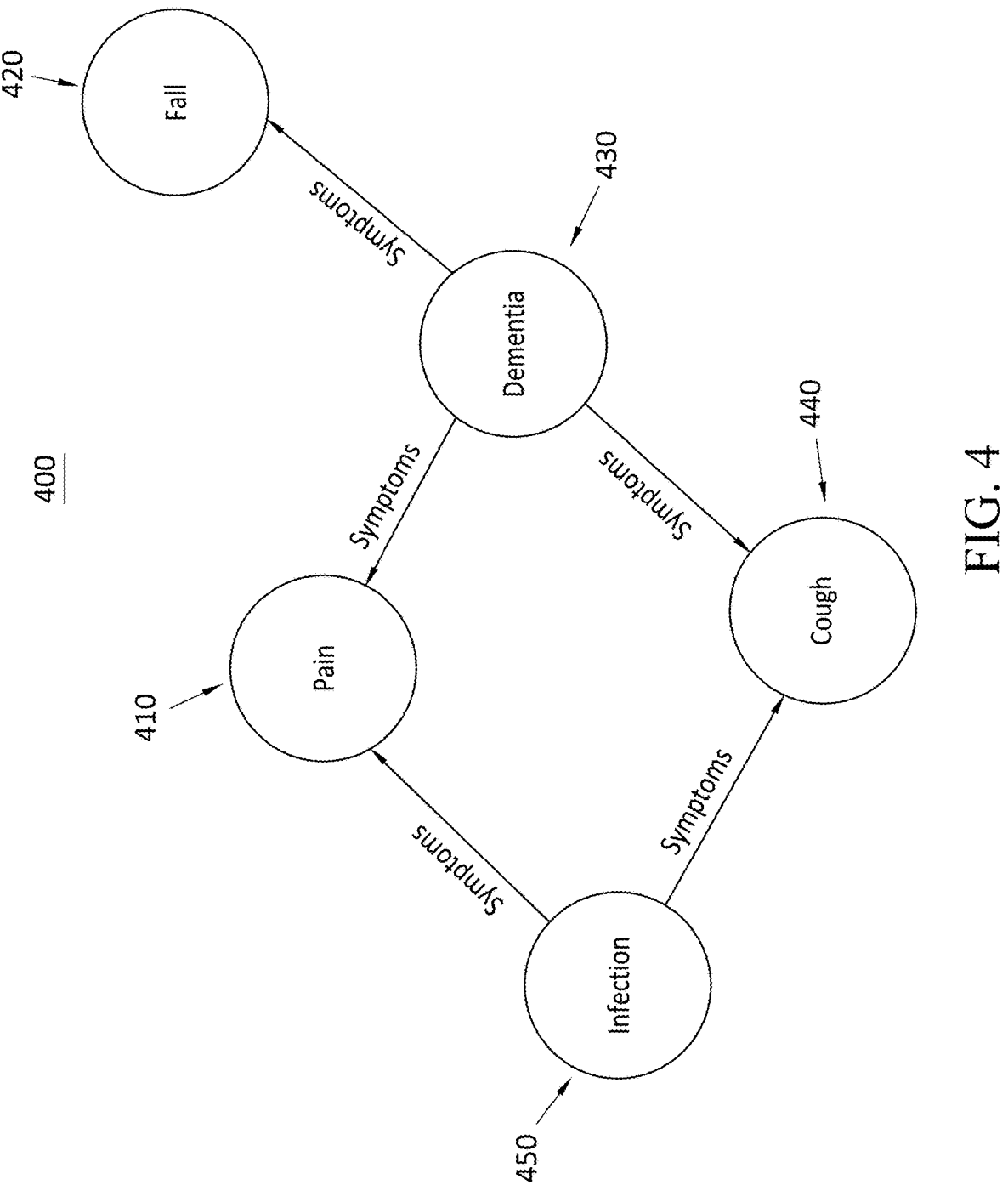
FIG. 4 illustrates an exemplary graph to determine a differential diagnosis, according to an embodiment.

Turning ahead in the drawings, FIG. 4 illustrates an exemplary graph 400 used to determine a differential diagnosis based on one or more symptoms associated with one or more diseases and/or medical conditions, according to an embodiment. Graph 400 is merely exemplary and is not limited to the embodiments presented herein. The graph can be employed in many different embodiments or examples not specifically depicted or described herein. In several embodiments, graph 400 can be an undirected graph with nodes representing medical conditions and symptoms related to the medical conditions. The nodes can include nodes 410, 420, 430, 440, and/or 450. Nodes 410 (pain), 420 (fall), and 440 (cough) are symptoms, and nodes 430 (dementia) and 450 (infection) are medical conditions (shown in bold). In several embodiments, graph 400 can include edges that connect the nodes (e.g., diseases or symptoms) on the graph illustrating a relationship between the disease and symptom.

In various embodiments, identifying the possible diseases associated with a given disease can include using a graph (e.g., 400) to capture all or a part of the relationships across different symptoms and diseases. In some embodiments, graph 400 can be used to determine a differential diagnosis by analysing two or more symptoms presented or disclosed by a user connected to two or more potential diseases. In various embodiments, each node in graph 400 can be associated with a corresponding Unified Medical Language System (UMLS) code, a name, and/or a unique identification code to identify an entity, such as a medical condition, a diseases, or a symptom.

For example, a patient can interact with a bot to disclose symptoms of pain and a cough. Based on two symptoms, without more evidence, graph 400 can be used to identify two potential entities or diseases, such as dementia (node 430) or infection (node 450). In this example, node 430 (dementia) can be connected by an edge to node 410 (pain) and by an edge to node 440 (cough). In following this example, node 450 (infection) also can be connected by an edge to node 410 (pain) and by an edge to node 440 (cough). Following this example, if the patient discloses another symptom in addition to pain (node 410) and cough (node 440), such as a fall (node 420), then dementia (node 430) can be a stronger probability associated with a disease.

Figure 5:
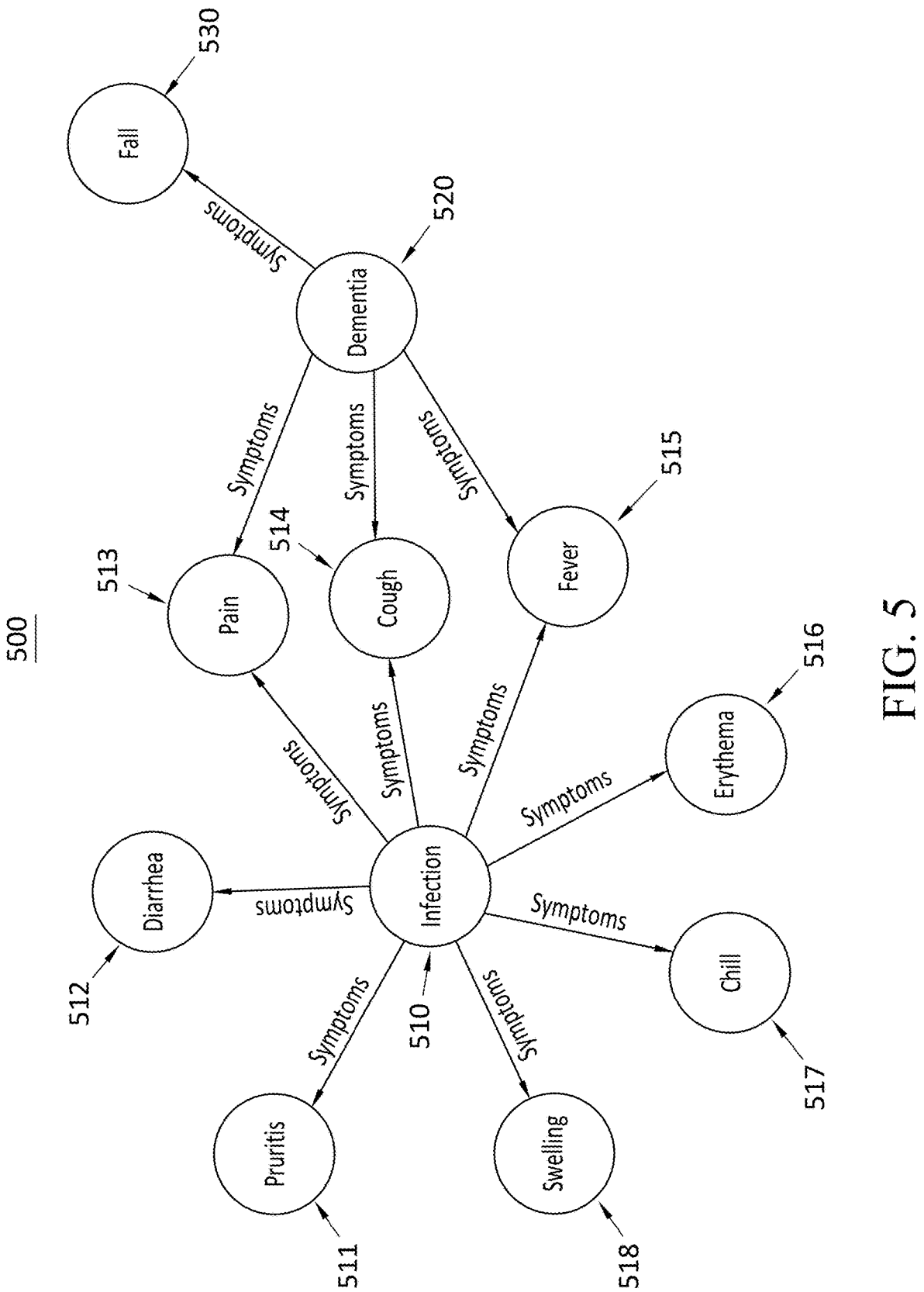
FIG. 5 illustrates a graph of a question generator, according to an embodiment.

Referring to the drawings, FIG. 5 illustrates a graph 500, which can be used by a question generator. In many embodiments, graph 500 can be used to generate one or more questions based on evidence to create a hypothesis diagnosis, according to an embodiment. Graph 500 is merely exemplary and is not limited to the embodiments presented herein. The graph 500 can be employed in many different embodiments or examples not specifically depicted or described herein.

In a number of embodiments, graph 500 can include a nodes that represent medical conditions (shown in bold), such as node 510 (infection) and a node 520 (dementia). In some embodiments, graph 500 also can include symptoms such as node 511 (pruritus), node 512 (diarrhea), node 513 of (pain), node 514 (cough), node 515 (fever), node 516 (erythema), node 517 (chill), node 518 (swelling), and node 530 (a fall). In several embodiments, graph 500 also can include edges that connect the nodes. Similar to graph 400 (FIG. 4, described above), the edges can connect diseases with related or recognized symptoms on graph 500.

In various embodiments, a question generator uses the relationships between each of the nodes to generate potential questions to send to the patient. Such a relationship between nodes can point to a most probable disease (e.g., infection) based on two recognized symptoms where several other symptoms related to infection are not yet recognized. For example, a first hypothesis can indicate a differential diagnosis in that two most probable diseases can include infection (node 510) or dementia (node 520). In some embodiments, graph 500 illustrates a relationship between recognized symptoms and a disease, thus other symptoms most often associated with infection (node 510) can include node 517 (chill) or node 518 (swelling). In several embodiments, question generator can generate questions asking whether a chill or swelling are also symptoms experienced by the patient. If true, the probability can point to infection as a possible disease diagnosis. If false, another disease can be explored likely ruling infection out.

Figure 6:
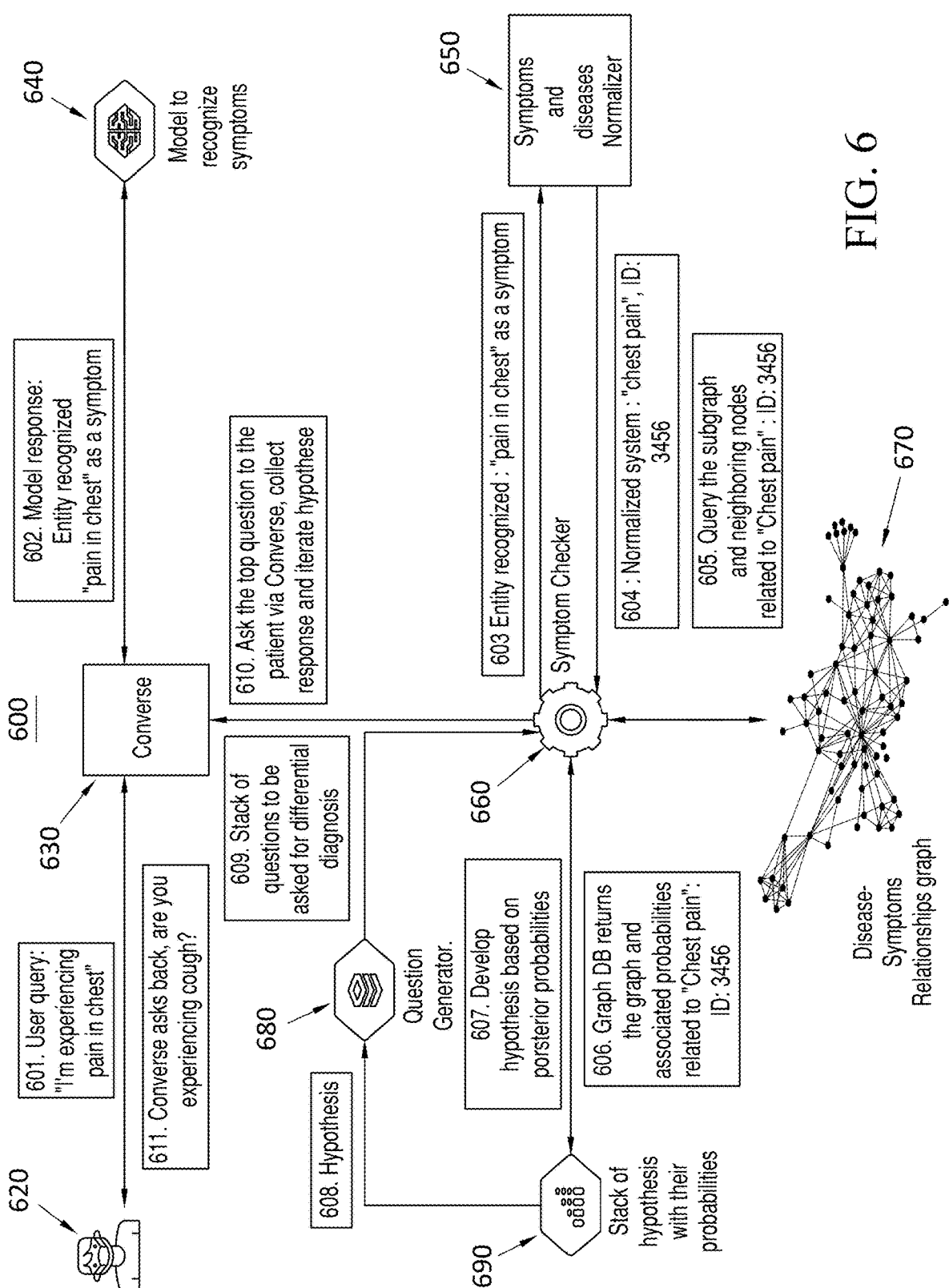
FIG. 6 illustrates a flow chart for a guided conversation, according to an embodiment.

Referring to the drawings, FIG. 6 illustrates a flow chart for a method 600 of a guided conversation with a conversational artificial intelligence, according to an embodiment. Method 600 is merely exemplary and is not limited to the embodiments presented herein. Method 600 can be employed in many different embodiments or examples not specifically depicted or described herein. In some embodiments, the procedures, the processes, and/or the activities of method 600 can be performed in the order presented. In other embodiments, the procedures, the processes, and/or the activities of method 600 can be performed in any suitable order. In still other embodiments, one or more of the procedures, the processes, and/or the activities of method 600 can be combined or skipped.

In some embodiments, method 600 can include activity 601 of a user 620 sending a user query to a converse system 630. User 620 can be similar or identical to user 350 or 351 (FIG. 3), which can use user computer 340 or 341 (FIG. 3). For example, a user query can include "I'm experiencing pain in my chest." In many embodiments, activity 601 can be implemented as described below in connection with activity 705 (FIG. 7).

In various embodiments, converse system 630 can provide a chat bot, which can receive and/or send data with user 620, a symptom recognition model 640 and/or a symptom checker system 660. In some embodiments, method 600 can proceed after activity 601 to an activity 602.

In some embodiments, method 600 can include activity 602 of converse system 630 querying symptom recognition model 640 to recognize an entity as a symptom. For example, the entity can be recognized "pain in my chest" as a symptom. In several embodiments, activity 602 can be implemented as described below in connection with activities 710, 715, and 720 (FIG. 7).

In various embodiments, symptom recognition model 640 can recognize symptoms from a query. In several embodiments, method 600 can proceed after activity 602 to an activity 603. In several embodiments, method 600 can include activity 603 of converse system 630 transmitting the entity recognized by symptom recognition model 640 to symptom checker system 660 as intake evidence. In some embodiments, activity 603 can be implemented as described below in connection with activities 710 and 725 (FIG. 7).

In some embodiments, symptom checker system 660 can analyze symptoms received as evidence. In several embodiments, symptom checker system 660 can receive and/or send data with converse system 630, a normalizer system 650, a question generator system 680, and a hypothesis data store 690.

In various embodiments, normalizing system 650 can normalize multiple symptoms and diseases to be used by symptom checker system 660. In some embodiments, method 600 can proceed after activity 603 to an activity 604.

In several embodiments, method 600 can include activity 604 of symptom checker system 660 querying normalizer system 650 with the entity to receive a normalized code for a recognized symptom. For example, a normalized symptom such as "chest pain" can include a normalized identification code that can be recognized by symptom checker system 660. In various embodiments, method 600 can proceed after activity 604 to an activity 605. In many embodiments, activity 604 can be implemented as described below in connection with activities 710 and 715 (FIG. 7).

In some embodiments, method 600 can include activity 605 of symptom checker system 660 using a subgraph 670 having neighboring nodes related to a recognized symptom. For example, querying a subgraph by using a normalized identification code for "chest pain" to determine connected edges to medical conditions, such as a disease. In many embodiments, activity 605 can be implemented as described below in connection with activities 720 and 725 (FIG. 7).

In various embodiments, subgraph 670 can be an undirected graph based on relationships between a disease and multiple symptoms. In some embodiments, method 600 can proceed from activity 605 to an activity 606.

In several embodiments, method 600 can include activity 606 of symptom checker system 660 determining associated probabilities from subgraph 670. For example, the undirected graph can return associated probabilities related to "chest pain." In various embodiments, method 600 can proceed from activity 606 to an activity 607. In many embodiments, activity 606 can be implemented as described below in connection with activities 720, 725, and 740 (FIG. 7).

In various embodiments, method 600 can include activity 607 of system checker 660 developing and sending hypotheses based on posterior probabilities to be stored in hypothesis data store 690. In many embodiments, activity 607 can be implemented as described below in connection with activities 715, 725 and 740 (FIG. 7).

In several embodiments, hypothesis data store 690 can store a stack of hypotheses with respective probabilities. In many embodiments, method 600 can proceed after activity 607 to an activity 608.

In various embodiments, method 600 can include activity 608 of question generator system 680 querying hypotheses from hypothesis data store 690.

In several embodiments, question generator 680 can generate questions using a question generator. In some embodiments, question generator system 680 can include intake of evidence received from the iterative process. In various embodiments, method 600 can proceed after activity 608 to an activity 609.

In some embodiments, method 600 can include activity 609 of question generator system 680 sending a stack of ranked stack of questions for the patient to symptom checker system 660 for a differential diagnosis. In many embodiments, method 600 can proceed from activity 609 to activity 610. In many embodiments, activity 609 can be implemented as described below in connection with activities 725 and 740 (FIG. 7).

In several embodiments, method 600 can include activity 610 of symptom checker system 660 asking the top questions to a patient via converse system 630 (e.g., chat bot) using an iterative process. In some embodiments, method 600 can proceed after activity 610 to an activity 611. In many embodiments, activity 610 can be implemented as described below in connection with activities 725 and 730 (FIG. 7).

In various embodiments, method 600 can include activity 611 of converse system 630 sending questions to user 620 based on symptoms related to a differential diagnosis. For example, such a question can include "Are you experiencing a cough?" In many embodiments, activity 611 can be implemented as described below in connection with activities 725 and 740 (FIG. 7).

Turning ahead in the drawings, FIG. 7 illustrates a flow chart for a method 700, according to another embodiment. In some embodiments, method 700 can be a method of determining a differential diagnosis based on one or more symptoms associated with one or more diseases and/or medical conditions. Method 700 is merely exemplary and is not limited to the embodiments presented herein. Method 700 can be employed in many different embodiments and/or examples not specifically depicted or described herein. In some embodiments, the procedures, the processes, and/or the activities of method 700 can be performed in the order presented. In other embodiments, the procedures, the processes, and/or the activities of method 700 can be performed in any suitable order. In still other embodiments, one or more of the procedures, the processes, and/or the activities of method 700 can be combined or skipped. In several embodiments, system 300 (FIG. 3) can be suitable to perform method 700 and/or one or more of the activities of method 700.

In these or other embodiments, one or more of the activities of method 700 can be implemented as one or more computing instructions configured to run at one or more processors and configured to be stored at one or more non-transitory computer-readable media. Such non-transitory computer-readable media can be part of a computer system such as symptom checker system 310 and/or web server 320. The processor(s) can be similar or identical to the processor(s) described above with respect to computer system 100 (FIG. 1).

In several embodiments, method 700 can include an activity 705 of receiving text from a user. In some embodiments, the text can include one or more symptoms. In various embodiments, receiving text can be from a mobile electronic device from the user.

In a number of embodiments, method 700 optionally or alternatively can include an activity 710 of translating the text received from the user into one or more codes for the one or more symptoms. In several embodiments, activity 710 optionally can include recognizing one or more symptom entities related to the one or more symptoms in the text using a clinical BERT model. In some embodiments, the clinical BERT model can include pre-trained (e.g., training data) from text received from multiple types of notes originating from open source data sets, such as MIMIC-2 million notes. In many embodiments, the clinical BERT model can be used as a specific language model for any language model. In various embodiments, an advantage of using a clinical BERT model can include the ability to fine tune the model in order to recognize symptom related entities from text using typical modelling techniques such as Sequence Labelling, Named-entity recognition. As another advantage, once the Bert Model is trained, the Bert model can assign categorical label (e.g., symptom) to each word. In many embodiments, each work of the words assigned as symptoms can be extracted out as symptom entities based on a corresponding order of occurrence in the original sentence (e.g., text).

In various embodiments, activity 710 further can include mapping the one or more symptom entities to the one or more codes. In several embodiments, activity 710 additionally can include mapping of one or more symptom entities to the codes using a Symptoms and Diseases Normalizer sub-system (e.g., querying normalizer system). The symptoms and diseases normalizer sub-system can be similar or identical to the activities of the querying normalizer system of activity 650 (FIG. 6.) In many embodiments, such a sub-system can infer the mapping based on the semantic similarity between the symptom entities and the description/definition of symptom codes. In some embodiments, mapping can also be performed via an elastic search, such as measuring the Damerau-Levenshtein distance between the symptom entities and symptom code names (e.g., descriptions).

In some embodiments, the clinical BERT model can be fine-tuned using a cross-entropy loss function to recognize multiple entities related to symptoms. In several embodiments, using cross-Entropy as a loss function to minimize the gap between the prediction from the model and the ground truth. In various embodiments, the loss function can be expressed within the prediction model in equation 1:

$$L(\theta) = -1/N * \Sigma \alpha \cdot y \log(\hat{y}) + \beta \cdot (1-y) \log(1-\hat{y}) \tag{1}$$

where, ŷs refers to the prediction from model, y refers to the ground truth, $\theta$ refers to parameters of loss function. 1/N, refers to number of data points, $\alpha$ refers to weight of loss function corresponding to class y, $\beta$ refers to refers to weight of loss function corresponding to class (1−y). In many embodiments, an advantage to fine-tuning the prediction model can be that the model can readily recognize the entities related to symptoms. In various embodiments, such as a fine-tuning approach, can serve two advantages. First, find-tuning can leverage the massive language vocabulary with increased language comprehension that can be inherently represented by language models, such as, bio-BERT, clinical-BERT, GPT, Chat-GPT, and/or another suitable language mode. Second, by using the fine-tuning approach, millions of dollars in training costs can be saved because fine-tuning re-uses previous learnings reconfigured as new data from respective language models. Additionally, fine-tuning can re-train the new or reconfigured data from previous outputs of previous learning to address specific objectives without having to re-learn the data or re-train the model (e.g., teach) and starting over each time from scratch. As an example, a language model, such as clinical-BERT, often never needs to be trained for specific tasks such as identifying pharmaceutical drug names from a text and/or textual format. In following this example, the clinical-Bert model and/or another language model can be trained for specific tasks after fine-tuning the model with labelled examples and/or synthetically generated examples.

In several embodiments, mapping the one or more symptom entities to the one or more codes additionally can include measuring a Damerau-Levenshtein distance between two strings. In various embodiments, the two strings can include one of the one or more symptom entities and a standard medical concept of a collection of standardized medical concepts. In some embodiments, an advantage over conventional mapping systems can include that this approach is more scalable and can increase the speed in processing millions of medical concepts while mapping the most likely medical concept relevant to a particular symptom entity.

In many embodiments, mapping the one or more symptom entities to the one or more codes additionally can include selecting one of the collection of standardized medical concepts can be based on the Damerau-Levenshtein distance between the two strings. In various embodiments, mapping recognized entities into standard UMLS codes can use 2 approaches: (i) an elastic search and (ii) a nearest neighbor search.

In a number of embodiments, using elastic search can include storing (e.g., holding) a large collection of standard medical concepts. In various embodiments, during elastic search, a recognized entity can be matched across these concepts using Damerau-Levenshtein distance. In several embodiments, the closest distance between a recognized entity and a concept can be selected. In some embodiments, Damerau-Levenshtein distance between two strings a (recognized entity), b (UMLS/a medical concept), can define a function $d_{a,b}(i,j)$, where the value of the function can be a distance between an i—symbol prefix of string a and a j-symbol prefix of b, as expressed in the function 1, below:

$$d_{a,b}(i,j) = \min \begin{cases} 0 & \text{if } i = j = 0, \quad (1) \\ d_{a,b}(i-1,j)+1 & \text{if } i > 0, \\ d_{a,b}(i,j-1)+1 & \text{if } j > 0, \\ d_{a,b}(i-1,j-)+1_{(a_i \neq b_j)} & \text{if } i,j > 0, \\ d_{a,b}(i-2,j-2)+1 & \begin{array}{l} \text{if } i,j > \text{ and} \\ a_i = b_{j-1} \text{ and } a_{i-1} = b_j \end{array} \end{cases}$$

where, d refers to Damerau-Levenshtein distance, i refers to length of a, j refers length of b, a and b are 2 strings used to evaluate the distance between them.

In a number of embodiments, using a Nearest Neighbor search approach to map recognized entities into standard UMLS codes also can include an equation 1, as expressed:

$$d(p,q) = \sqrt{\sum_{i=1}^{n} (q_i - p_i)^2}$$

where, q refers to an embedding vector of a recognized entity from the model, p refers to another embedding vector of known medical concepts, d refers to Euclidean distance, and i refers to dimension along which the distance is calculated In some embodiments, using the Nearest Neighbor approach can include capturing the distance between these (p, q). In several embodiments, calculating a distance can include using either an elastic search approach or a Nearest Neighbors approach to generate a most likely standard medical concept that is closest to a given query.

In several embodiments, mapping the one or more symptom entities to the one or more codes also can include retrieving a code for the one of the collection of standardized medical concepts. In various embodiments, mapping the one or more symptom entities further can use the nearest neighbor approach. As an example, the q(symptom entity) needs to be mapped to the nearest p (medical concept) by which several methods can be used including the nearest neighbor search or a linear search. In some embodiments, solving q to be mapped to p using the linear search, can include searching over an entire space to find the nearest point p that is closest to q. In several embodiments, another efficient mapping approach can include using a locally sensitive hashing approach where the entire search space is grouped into buckets based on a similarity metric, such as semantic similarity. In some embodiments, using the locally sensitive hashing approach can include performing a search using approximation as a practical approach when the number of medical concepts is extremely large. In such an approximation approach, first finding the relevant bucket and then searching all the entries in that bucket.

In various embodiments, mapping the one or more symptom entities to the one or more codes of further can include embedding a first vector for one of the one or more symptom entities. In some embodiments, generating embedding vectors for each of the symptom entities can be performed (e.g., transformed) using a language model, such as Clinical BERT. In several embodiments, language models can be trained on training data based on voluminous historical medical texts and/or literature on objectives, such models can include Masked Language Modelling or Replaced Token Detection, which forces the model to internalize the medical concepts, terminologies etc. In many embodiments, transforming one or more codes, texts, and/or images can include embedding a vector as an internal representation of a symptom entity to be used as input into training data that can train machine learning models based on inputs of symptom entities. In several embodiments, language models can include an encoder component and a decoder component in their respective architecture. In various embodiments, generating or transforming codes into embedded vectors can include inputting historical records or data of the symptom entities and storing the output of the vectors using the encoder feature of such language models.

In some embodiments, mapping the one or more symptom entities to the one or more codes additionally can include embedding a second vector for a standard medical concept of a collection of standardized medical concepts.

In various embodiments, mapping the one or more symptom entities to the one or more codes also can include calculating a distance between the first vector and the second vector. In some embodiments, calculating the distance can include interpreting the distance between a first vector and a second vector as a metric of irrelevancy. In several embodiments, the smaller the metric of irrelevancy between a first vector and a second vector, the higher the likelihood that both vectors are related and/or relevant to each other. Conversely, if the distance is high, then they are very dissimilar entities/concepts. Thus calculating the distance (metric of irrelevancy) measure can assist in solving the problem of relevancy by performing simple numerical comparisons.

In many embodiments, mapping the one or more symptom entities to the one or more codes further can include selecting one of the collection of standardized medical concepts based on the distance.

In several embodiments, mapping the one or more symptom entities to the one or more codes additionally can include retrieving a code for the one of the collection of standardized medical concepts.

In some embodiments, method 700 also can include activity 715 of generating, from an undirected graph, a subgraph mapping the one or more symptoms to connected diseases. In several embodiments, the nodes of the undirected graph can include diseases and symptoms, such an undirected graph can be similar or identical to graph 400 (FIG. 4). In various embodiments, activity 715 can include identifying the neighboring diseases given a set of observed symptoms. In some embodiments, identifying the possible diseases associated with a given disease can include analysis using the undirected graph to capture the relationships across different entities symptoms and diseases. In many embodiments, activity 715 can be implemented as described above in connection with FIG. 4.

In various embodiments, activity 715 of generating the subgraph further can include building a minimum spanning path across the one or more symptoms in the undirected graph.

In some embodiments, activity 715 also can include identifying the connected diseases based on relationships between the diseases and the symptoms in the undirected graph.

In a number of embodiments, method 700 also can include an activity 720 of calculating (a) a respective posterior probability for each of the connected diseases using the subgraph and (b) a hypothesis diagnosis based on evidence of one or more symptoms. The evidence can include the one or more symptoms.

In some embodiments, recalculating the posterior probability of neighboring diseases can be triggered when one or more symptoms are recognized. In several embodiments, initially a set of symptoms can be presented by the user, s1, s2, s3 . . . si, where s refers to a symptom. In some embodiments, the set of symptoms can include a set of most frequently presented symptoms. In various embodiments, after receiving the set of symptoms, the conversational assistant or chat bot can guide the conversation to figure out an accurate disease diagnosis.

In several embodiments, a symptom checker can (i) build a minimum spanning path that can span across s1, s2, s3 . . . si and (ii) identify several the connected diseases with symptoms based on a relationship of a connected diseases and one or more symptoms using an undirected graph, such as an exemplary graph G. Graph G can be similar or identical to Graph 400 (FIG. 4).

In some embodiments, a conversational assistant or chat bot can operate on an undirected graph, such graph G and probe the nodes and symptoms for further questions to send to the user.

In several embodiments, activity 720 can calculates the probabilities of most likely diseases d1, d2, d3, . . . dj from the graph using a Bayesian way, where dj represents a given disease. Calculating the probabilities in a Bayesian way can be expressed as equation 1, as follows:

$$P(dj \mid \text{Evidence}) = \frac{P(dj)^* P(\text{Evidence} \mid dj)}{\sum P(dk)^* P(\text{Evidence} \mid dk)} \forall \, dk \in G \quad (1)$$

where, P(dk) refers to the prior probability of occurrence of a disease k,

P(dj|Evidence) refers to the posterior probability of occurrence of disease dj, given the evidence, and P(Evidence| dj) refers to the conditional probability of evidence to show up, given a disease dj. In several embodiments, after calculating the P(dj|Evidence) for the possible diseases, then sort the possible diseases based on the probabilities in a hierarchical order where, a most probable disease stacks on top of the stack.

In various embodiments, updating a current hypothesis when a disease "dj" is listed on top of the stack indicating a highest probability over other diseases being the most likely disease given the symptoms.

In some embodiments, a symptom checker can present an updated hypothesis based on a history of conversation with the user. Such an updated hypothesis can be used by the questions generator to fetch one or more questions to send to the patient. In many embodiments, activity 725, 730 and 740 can be implemented as described above in connection with FIG. 5.

In several embodiments, activity 720 can include using multiple activities and/or iterations to calculate a posterior probability for each of the connected diseases to formulate a hypothesis diagnosis. Such multiple activities can include an activity 725, an activity 730, an activity 735, and an activity 740, as described below in further detail, which in some embodiments can be iteratively performed.

In various embodiments, activity 720 can include activity 725 of determining one or more questions to send to the user based on a set of top symptoms for the hypothesis diagnosis.

In various embodiments, activity 725 can include guiding the conversation with a user to determine a differential diagnosis by analyzing a condition of a user (e.g., patient). In several embodiments, differential diagnosis can identify the presence of a disease entity where multiple alternatives are possible. In some embodiments, activity 725 can include a process of obtaining additional information from the user that can reduce the search space of the possible diseases given the symptoms in a probabilistic approach. In a number of embodiments, activity 725 can use evidence such as symptoms from a patient and medical knowledge to adjust probabilities of disease entities and re-direct the conversation to arrive at a disease diagnosis and/or recommend the user schedule an appointment with a provider.

As an example of a chat bot engaging in a guided conversation with the patient can include an iterative process of receiving information and asking questions to help arrive at to the most probable disease diagnoses. For example, a guided conversation between a patient and a conversational artificial intelligence or chat bot ("bot") can include an iterative process of receiving responses and asking questions to arrive at a most probable disease diagnosis or to recommend scheduling an appointment with a provider.

For example, a patient texts or asks a chat bot via an online platform: "I'm dealing with Pain and Cough." Since there can be many possible diseases that could cause Pain, such as, an infection, osteoporosis, pneumonia, or another suitable disease, where symptoms can include pain, which can be ambiguous. In this example, a process of eliminating each disease that includes pain can be a time-consuming task without ever arriving at a diagnosis.

In a number of embodiments, using a differential diagnosis approach can be advantageous. In this example, the conversation assistant or chat bot can develop a hypotheses based on a number of possible diseases or medical conditions connected to the undirected graph, such as graph 400. In following this example, updating each hypotheses space during each iteration can include asking the right questions based on additional incoming responses from the patient as an evidence.

In some embodiments, activity 725 can include finding first symptoms of the one or more symptoms within the subgraph that are associated with the hypothesis diagnosis.

In several embodiments, activity 725 also can include ranking the first symptoms based on one or more of the respective posterior probabilities to determine the set of top symptoms.

In various embodiments, activity 725 further can include selecting the one or more questions based on the set of top symptoms. In several embodiments, selecting the one or more questions can include using the question generator to re-rank each of the connected symptoms to a most probable disease or a differential diagnosis based on each symptoms probability of occurrence.

In this example, the question generator sends one or more questions to the patient based on the top symptoms. Such an exemplary question from the chat bot to the patient can include "You might be experiencing an infection or dementia. Are you also experiencing a chill or swelling?" In following with this example, receiving a response such as yes to experiencing a chill but no to experiencing swelling forms the evidence used to update a current hypothesis. In this example, at a certain point, a recommendation to schedule an appointment with a provider is sent to the patient.

In several embodiments, a question generator, can receive a hypothesis of a differential diagnosis or a disease based on evidence "E", such as symptoms. In some embodiments, the question generator can iteratively receive one or more updated hypotheses based on additional evidence received, such as a response from a patient to a question sent by the chat bot. For example, a hypothesis can include a given disease "dj" as being a most likely disease based on a number of iterations and a number of additional symptoms received (e.g., past conversation history). In a number of embodiments, the question generator explores graph 500 to locate all of the possible symptoms associated with dj and re-ranks each of the symptoms in a hierarchical order based on probabilities of each disease: sj1, sj2, sj3 . . . sjn and picks a top N questions to send to the patient to the conversational assistant or chat bot. In many embodiments, the top N questions can be a configurable parameter.

In various embodiments, the chat bot selects the top questions to send to the patient, receives one or more responses, gathers additional evidence, and updates the posterior probabilities of each disease before updating the current hypothesis.

In various embodiments, activity 720 additionally can include activity 730 of sending the one or more questions to the user.

In some embodiments, activity 720 also can include activity 735 of receiving one or more responses from the user in response to the one or more questions.

In a number of embodiments, activity 720 further can activity 740 of updating the hypothesis diagnosis based on the one or more responses.

In some embodiments, activity 740 additionally can include recalculating the respective posterior probability for each of the connected diseases using the subgraph and the evidence, as updated, by the one or more responses. In several embodiments, activity 740 can include a iterative process to update the hypothesis diagnosis. Such iterative process can use reconfigured data from a previous iteration as input to another iteration until a predetermined maximum number of iterations have been conducted. In many embodiments, a previous iteration can include another hypothesis diagnosis that can be reconfigured into a new hypothesis diagnosis as output in the current iteration and so forth. In several embodiments, reconfigured data can eliminate a former hypothesis diagnosis based on additional input, bolster or confirm a former hypothesis diagnosis based on addition input, and/or modifying a previous hypothesis diagnosis in favor of a secondary hypothesis diagnosis based on each iteration using additional input. Each set of data or set of reconfigured data iteration can be used as training data for subsequent iterations where the system learns cumulatively from prior outputs of prior iterations.

In various embodiments, activity 740 also can include selecting one of the connected diseases as the hypothesis diagnosis based on one or more of the respective posterior probabilities. In an example, assume a current hypothesis output can be a common cold based on the previous responses of the user describing symptoms, such as sneezing. In following this example, if the patient reveals that the patient is also suffering additional and/or new symptoms such as diarrhea and/or a loss of taste, then hypothesis diagnosis can be reconfigured as new data outputting a different disease and/or a cause for the illness such as Covid-19 as a probable hypotheses based on its posterior probability from the new evidence and/or symptoms collectively.

In some embodiments, method 700 further can include an activity 745 of sending a recommendation to the user to schedule an appointment with a provider for the hypothesis diagnosis, as updated.

Returning to FIG. 3, in a number of embodiments, communication system 311 can at least partially perform activity 601 (FIG. 6) of a user 620 (FIG. 6) sending a user query to a converse system 630, activity 603 (FIG. 6) of converse system 630 (FIG. 6) transmitting the entity recognized by symptom recognition model 640 (FIG. 6) to symptom checker system 660 as intake evidence, activity 611 (FIG. 6) of converse system 630 (FIG. 6) sending questions to user 620 (FIG. 6) based on symptoms related to a differential diagnosis, activity 705 (FIG. 7) of receiving text from a user, activity 730 (FIG. 7) of sending the one or more questions to the user, and/or activity 735 (FIG. 7) of receiving one or more responses from the user in response to the one or more questions.

In various embodiments, generating system 312 can at least partially perform activity 608 (FIG. 6) of question generator system 680 (FIG. 6) querying hypotheses from hypothesis data store 690 (FIG. 6), activity 715 (FIG. 7) of generating, from an undirected graph, a subgraph mapping the one or more symptoms to connected diseases.

In several embodiments, calculating system 313 can at least partially perform activity 606 (FIG. 6) of symptom checker system 660 (FIG. 6) determining associated probabilities from subgraph 670 (FIG. 6), and/or activity 720 (FIG. 7) of calculating a respective posterior probability for each of the connected diseases using the subgraph and evidence to formulate a hypothesis diagnosis.

In many embodiments, translating system 314 can at least partially perform activity 710 (FIG. 7) of translating the text received from the user into one or more codes for the one or more symptoms.

In some embodiments, mapping system 315 can at least partially perform activity 604 (FIG. 6) of symptom checker system 660 (FIG. 6) querying normalizer system 650 (FIG. 6) with the entity to receive a normalized code for a recognized symptom, and/or 715 (FIG. 7) of generating, from an undirected graph, a subgraph mapping the one or more symptoms to connected diseases.

In several embodiments, hypothesizing system 316 can at least partially perform activity 607 (FIG. 6) of system checker 660 (FIG. 6) developing and sending hypotheses based on posterior probabilities to be stored in hypothesis data store 690 (FIG. 6), activity 725 (FIG. 7) of determining one or more questions to send the user based on a set of top symptoms for the hypothesis diagnosis, activity 740 (FIG. 7) of updating the hypothesis diagnosis based on the one or more responses, and/or activity 745 (FIG. 7) of sending a recommendation to the user to schedule an appointment with a provider for the hypothesis diagnosis Analyzing system 318 can at least partially perform activity 602 (FIG. 6) of converse system 630 (FIG. 6) querying symptom recognition model 640 (FIG. 6) to recognizing an entity as a symptom Graphing system 319 can at least partially perform activity 605 (FIG. 6) of symptom checker system 660 (FIG. 6) using a subgraph 670 (FIG. 6) having neighboring nodes related to a recognized symptom, activity 609 (FIG. 6) of question generator system 680 (FIG. 6) sending a stack of ranked stack of questions for the patient to symptom checker system 660 (FIG. 6) for a differential diagnosis, and/or activity 610 (FIG. 6) of symptom checker system 660 (FIG. 6) asking the top questions to a patient via converse system 630 (e.g., chat bot) using an iterative process.

In several embodiments, web server 320 can include a web page system 321. Web page system 321 can at least partially perform sending instructions to user computers (e.g., 340-341) based on information received from communication system 311.

Various embodiments can include a system including one or more processors and one or more non-transitory computer-readable media storing computing instructions that, when executed on the one or more processors, cause the one or more processors to perform certain acts. The acts can include receiving text from a user. The text can include one or more symptoms. The acts also can include generating, from an undirected graph, a subgraph mapping the one or more symptoms to connected diseases. The nodes of the undirected graph can include diseases and symptoms. The acts further can include calculating (a) a respective posterior probability for each of the connected diseases using the subgraph and (b) a hypothesis diagnosis based on evidence of one or more symptoms. The evidence can include the one or more symptoms. Iteratively, the acts also can include determining one or more questions to send to the user based on a set of top symptoms for the hypothesis diagnosis. Iteratively, the acts further can include sending the one or more questions to the user. Iteratively, the acts additionally can include receiving one or more responses from the user in response to the one or more questions. Iteratively, the acts further can include updating the hypothesis diagnosis based on the one or more responses. The acts also can include sending a recommendation to the user to schedule an appointment with a provider for the hypothesis diagnosis, as updated.

A number of embodiments can include a method being implemented via execution of computing instructions configured to run at one or more processors and stored at one or more non-transitory computer-readable media. The method can include receiving text from a user. The text can include one or more symptoms. The method also can include generating, from an undirected graph, a subgraph mapping the one or more symptoms to connected diseases. The nodes of the undirected graph can include diseases and symptoms.

The method further can include calculating (a) a respective posterior probability for each of the connected diseases using the subgraph and (b) a hypothesis diagnosis based on evidence of one or more symptoms. The evidence can include the one or more symptoms. Iteratively, the acts also can include determining one or more questions to send to the user based on a set of top symptoms for the hypothesis diagnosis. Iteratively, the method also can include determining one or more questions to send to the user based on a set of top symptoms for the hypothesis diagnosis. Iteratively, the method further can include sending the one or more questions to the user. Iteratively, the method additionally can include receiving one or more responses from the user in response to the one or more questions. Iteratively, the method further can include updating the hypothesis diagnosis based on the one or more responses. The method also can include sending a recommendation to the user to schedule an appointment with a provider for the hypothesis diagnosis, as updated.

Although automatically determining a diagnosis during a conversation with a chat bot and a patient has been described with reference to specific embodiments, it will be understood by those skilled in the art that various changes may be made without departing from the spirit or scope of the disclosure. Accordingly, the disclosure of embodiments is intended to be illustrative of the scope of the disclosure and is not intended to be limiting. It is intended that the scope of the disclosure shall be limited only to the extent required by the appended claims. For example, to one of ordinary skill in the art, it will be readily apparent that any element of FIGS. 1-7 may be modified, and that the foregoing discussion of certain of these embodiments does not necessarily represent a complete description of all possible embodiments. For example, one or more of the procedures, processes, or activities of FIGS. 6-7 may include different procedures, processes, and/or activities and be performed by many different modules, in many different orders, and/or one or more of the procedures, processes, or activities of FIGS. 6-7 may include one or more of the procedures, processes, or activities of another different one of FIGS. 6-7. As another example, the systems within symptom checker system 310 and/or webserver 320 (see FIG. 3) can be interchanged or otherwise modified.

Replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. A system comprising:
one or more processors; and
one or more non-transitory computer-readable media storing computing instructions that, when executed on the one or more processors, cause the one or more processors to perform:

fine-tuning a clinical BERT model, using a cross-entropy loss function, to recognize symptom entities related to symptoms;

receiving text-based evidence from a user, wherein the text-based evidence comprises one or more of the symptoms;

translating the text-based evidence received from the user into one or more codes for the one or more of the symptoms, wherein the translating comprises:

recognizing one or more of the symptom entities related to the one or more of the symptoms in the text-based evidence, using the fine-tuned, clinical BERT model; and mapping the one or more of the symptom entities to the one or more codes;

generating, from an undirected graph, a subgraph mapping the one or more of the symptoms to connected diseases, wherein nodes of the undirected graph comprise diseases and symptoms;

receiving a history of conversation between the user and a question generator;

calculating (a) a respective posterior probability for each of the connected diseases, using the subgraph, and (b) a hypothesis diagnosis based on the text-based evidence; and iteratively and until a predetermined number of iterations are conducted:

determining one or more questions to send to the user based on a set of top symptoms for the hypothesis diagnosis;

sending the one or more questions to the user;

receiving one or more responses from the user in response to the one or more questions; and updating the hypothesis diagnosis based on the one or more responses and on the history of conversation between the user and the question generator; and sending a recommendation to the user to schedule an appointment with a provider for the updated hypothesis diagnosis, as updated.

2. The system of claim 1, wherein mapping the one or more of the symptom entities to the one or more codes further comprises:

measuring a Damerau-Levenshtein distance between two strings, wherein the two strings comprise one of the one or more of the symptom entities and a standard medical concept of a collection of standardized medical concepts;

selecting one of the collection of standardized medical concepts based on the Damerau-Levenshtein distance between the two strings; and retrieving a code for the one of the collection of standardized medical concepts.

3. The system of claim 1, wherein mapping the one or more of the symptom entities to the one or more codes further comprises:

embedding a first vector for one of the one or more of the symptom entities;

embedding a second vector for a standard medical concept of a collection of standardized medical concepts;

calculating a distance between the first vector and the second vector;

selecting one of the collection of standardized medical concepts based on the distance; and retrieving a code for the one of the collection of standardized medical concepts.

4. The system of claim 1, wherein generating the subgraph further comprises:

building a minimum spanning path across the one or more of the symptoms in the undirected graph; and identifying the connected diseases based on relationships between the diseases and the symptoms in the undirected graph.

5. The system of claim 1, wherein determining the one or more questions to send to the user based on the set of top symptoms for the hypothesis diagnosis further comprises:

finding first symptoms of the one or more of the symptoms within the subgraph that are associated with the hypothesis diagnosis;

ranking the first symptoms based on one or more of the respective posterior probabilities to determine the set of top symptoms; and selecting the one or more questions based on the set of top symptoms.

6. The system of claim 1, wherein updating the hypothesis diagnosis further comprises:

recalculating the respective posterior probability for each of the connected diseases using the subgraph, as updated, by the one or more responses.

7. The system of claim 6, wherein updating the hypothesis diagnosis further comprises:

selecting one of the connected diseases as the hypothesis diagnosis based on one or more of the respective posterior probabilities.

8. A method being implemented via execution of computing instructions configured to run on one or more processors and stored at one or more non-transitory computer-readable media, the method comprising:

fine-tuning a clinical BERT model, using a cross-entropy loss function, to recognize symptom entities related to symptoms;

receiving text-based evidence from a user, wherein the text-based evidence comprises one or more of the symptoms;

translating the text-based evidence received from the user into one or more codes for the one or more of the symptoms, wherein the translating comprises:

recognizing one or more of the symptom entities related to the one or more of the symptoms in the text-based evidence, using the fine-tuned, clinical BERT model; and mapping the one or more of the symptom entities to the one or more codes;

generating, from an undirected graph, a subgraph mapping the one or more of the symptoms to connected diseases, wherein nodes of the undirected graph comprise diseases and symptoms;

receiving a history of conversation between the user and a question generator;

calculating (a) a respective posterior probability for each of the connected diseases, using the subgraph, and (b) a hypothesis diagnosis based on the text-based evidence; and iteratively and until a predetermined number of iterations are conducted:

determining one or more questions to send to the user based on a set of top symptoms for the hypothesis diagnosis;

sending the one or more questions to the user;

receiving one or more responses from the user in response to the one or more questions; and updating the hypothesis diagnosis based on the one or more responses and on the history of conversation between the user and the question generator; and sending a recommendation to the user to schedule an appointment with a provider for the updated hypothesis diagnosis.

9. The method of claim 8, wherein mapping the one or more of the symptom entities to the one or more codes further comprises:

measuring a Damerau-Levenshtein distance between two strings, wherein the two strings comprise one of the one or more of the symptom entities and a standard medical concept of a collection of standardized medical concepts;

selecting one of the collection of standardized medical concepts based on the Damerau-Levenshtein distance between the two strings; and retrieving a code for the one of the collection of standardized medical concepts.

10. The method of claim 8, wherein mapping the one or more of the symptom entities to the one or more codes further comprises:

embedding a first vector for one of the one or more of the symptom entities;

embedding a second vector for a standard medical concept of a collection of standardized medical concepts;

calculating a distance between the first vector and the second vector;

selecting one of the collection of standardized medical concepts based on the distance; and retrieving a code for the one of the collection of standardized medical concepts.

11. The method of claim 8, wherein generating the subgraph further comprises:

building a minimum spanning path across the one or more of the symptoms in the undirected graph; and identifying the connected diseases based on relationships between the diseases and the symptoms in the undirected graph.

12. The method of claim 8, wherein determining the one or more questions to send the user based on the set of top symptoms for the hypothesis diagnosis further comprises:

finding first symptoms of the one or more of the symptoms within the subgraph that are associated with the hypothesis diagnosis;

ranking the first symptoms based on one or more of the respective posterior probabilities to determine the set of top symptoms; and selecting the one or more questions based on the set of top symptoms.

13. The method of claim 8, wherein updating the hypothesis diagnosis further comprises:

recalculating the respective posterior probability for each of the connected diseases using the subgraph, as updated, by the one or more responses.

14. The method of claim 13, wherein updating the hypothesis diagnosis further comprises:

selecting one of the connected diseases as the hypothesis diagnosis based on one or more of the respective posterior probabilities.

* * * * *